US010738267B2

(12) United States Patent
Lintula et al.

(10) Patent No.: US 10,738,267 B2
(45) Date of Patent: Aug. 11, 2020

(54) LIQUID LAUNDRY DETERGENT COMPOSITION COMPRISING A CORE/SHELL ENCAPSULATE

(71) Applicant: The Procter & Gamble Company, Cincinnati, OH (US)

(72) Inventors: Nea Janette Lintula, Brussels (BE); Jean-Pol Boutique, Gembloux (BE); Johan Smets, Lubbeek (BE); Laura Orlandini, Geneva (CH); Robby Renilde Francois Keuleers, Lippelo (BE)

(73) Assignee: The Procter & Gamble Company, Cincinnati, OH (US)

( * ) Notice: Subject to any disclaimer, the term of this patent is extended or adjusted under 35 U.S.C. 154(b) by 225 days.

(21) Appl. No.: 15/917,874

(22) Filed: Mar. 12, 2018

(65) Prior Publication Data

US 2018/0265816 A1 Sep. 20, 2018

(30) Foreign Application Priority Data

Mar. 16, 2017 (EP) .................................... 17161266

(51) Int. Cl.

| | |
|---|---|
| ***A61L 9/04*** | (2006.01) |
| ***C11D 3/50*** | (2006.01) |
| ***A61K 8/00*** | (2006.01) |
| ***C11D 3/30*** | (2006.01) |
| ***C11D 17/00*** | (2006.01) |
| ***C11D 17/04*** | (2006.01) |
| ***C11D 1/22*** | (2006.01) |
| ***C11D 3/04*** | (2006.01) |
| ***C11D 3/386*** | (2006.01) |
| ***C11D 1/14*** | (2006.01) |

(52) U.S. Cl.

CPC .............. *C11D 3/505* (2013.01); *C11D 1/143* (2013.01); *C11D 1/22* (2013.01); *C11D 3/04* (2013.01); *C11D 3/046* (2013.01); *C11D 3/30* (2013.01); *C11D 3/38672* (2013.01); *C11D 3/50* (2013.01); *C11D 17/0039* (2013.01); *C11D 17/043* (2013.01)

(58) Field of Classification Search

CPC .. C11D 3/505; C11D 3/30; C11D 3/04; C11D 3/046; C11D 3/38672; C11D 17/0039; C11D 17/043; C11D 1/143; C11D 1/043; C11D 3/50; C11D 7/043

USPC .......................................................... 512/4, 1

See application file for complete search history.

(56) References Cited

U.S. PATENT DOCUMENTS

| | | | | |
|---|---|---|---|---|
| 3,516,941 | A | 6/1970 | Matson | |
| 4,145,184 | A | 3/1979 | Brain et al. | |
| 4,675,352 | A | 6/1987 | Winter et al. | |
| 8,394,753 | B2 | 3/2013 | Wagner et al. | |
| 9,186,642 | B2 | 11/2015 | Dihora et al. | |
| 9,416,339 | B2 * | 8/2016 | Bianchetti ................ | C11D 3/30 |
| 2008/0096780 | A1 | 4/2008 | Veugelers et al. | |
| 2010/0040884 | A1 | 2/2010 | Smets et al. | |
| 2011/0076395 | A1 | 3/2011 | Sun et al. | |
| 2011/0268802 | A1 | 11/2011 | Dihora et al. | |
| 2012/0058929 | A1 | 3/2012 | Laubender et al. | |
| 2014/0323383 | A1 * | 10/2014 | Trujillo .............. | C11D 17/0039 510/439 |
| 2016/0166480 | A1 | 6/2016 | Lei et al. | |

FOREIGN PATENT DOCUMENTS

| | | | |
|---|---|---|---|
| WO | WO2010028907 | A1 | 3/2010 |
| WO | WO2014032920 | A1 | 3/2014 |
| WO | WO2016106362 | A1 | 6/2016 |

OTHER PUBLICATIONS

EP Search Report for application No. 17161267.4-1358, dated Apr. 9, 2017, 8 pages.
Search Report for application No. 17161266.6-1375, dated Sep. 8, 2017, 7 pages.

* cited by examiner

*Primary Examiner* — Jessica Whiteley
(74) *Attorney, Agent, or Firm* — Gregory S. Barley-Emerson

(57) ABSTRACT

The present invention relates to liquid laundry detergent compositions comprising core/shell encapsulates, water-soluble unit dose articles comprising said encapsulates and methods of using said compositions and unit dose articles.

19 Claims, No Drawings

LIQUID LAUNDRY DETERGENT COMPOSITION COMPRISING A CORE/SHELL ENCAPSULATE

FIELD OF THE INVENTION

The present invention relates to liquid laundry detergent compositions comprising core/shell encapsulates, water-soluble unit dose articles comprising said encapsulates and methods of using said compositions and unit dose articles.

BACKGROUND OF THE INVENTION

Liquid laundry detergent compositions comprise perfume materials and cleaning technologies. Preferably in order to provide both immediate and long term scent benefits on fabrics liquid detergent compositions comprise a mixture of encapsulated perfumes and free perfumes. To provide the preferred scent often the free perfumes comprise aldehydic and/or ketone perfume raw materials. Encapsulated perfumes preferably comprise a higher percentage of perfume raw materials with log P>3.0 to ensure leakage of the perfume out of the capsules is minimized.

However, in such liquid detergent compositions there is a tendency for the liquid detergent composition to discolour and/or for the encapsulates to leak the internal contents. This can negatively impact the consumer experience both from an aesthetic point of view and performance point of view, especially long lasting scent performance.

Therefore, there is a need in the art for a liquid laundry detergent composition that comprises aldehydic and/or ketone materials, core/shell encapsulates and which exhibits reduced discolouration and leakage from said encapsulates. It is also preferable to provide a liquid laundry detergent composition that comprises aldehydic and/or ketone materials, core/shell encapsulates and which exhibits reduced discolouration and leakage from said encapsulates and provide long lasting scent benefit on fabrics.

It was surprisingly found that the specific composition of the present invention overcame these problems.

SUMMARY OF THE INVENTION

A first aspect of the present invention is a liquid laundry detergent composition comprising;

a. a core/shell encapsulate, wherein the core comprises a benefit agent and wherein the shell comprises polyacrylate, polyurethane, polyurea or a mixture thereof;
b. free perfume, wherein the free perfume comprises an aldehydic perfume raw material, a ketone perfume raw material or a mixture thereof;
c. an alkanolamine;
d. sulphite;
e. a $C_{11-13}$ linear alkylbenzene sulphonate.

A second aspect of the present invention is a water-soluble unit dose article comprising a water-soluble film and a liquid laundry detergent composition according to the present invention, preferably wherein the water-soluble film comprises polyvinylalcohol.

A third aspect of the present invention is a process of washing fabrics comprising the steps of contacting the liquid laundry detergent composition or unit dose article according to the present invention with water such that the liquid laundry detergent composition is diluted in water by at least 400 fold to form a wash liquor, and contacting fabrics with said wash liquor.

DETAILED DESCRIPTION OF THE INVENTION

Liquid Laundry Detergent Composition

The present invention is to a liquid laundry detergent composition. The term 'liquid laundry detergent composition' refers to any laundry detergent composition comprising a liquid capable of wetting and treating a fabric, and includes, but is not limited to, liquids, gels, pastes, dispersions and the like. The liquid composition can include solids or gases in suitably subdivided form, but the liquid composition excludes forms which are non-fluid overall, such as tablets or granules.

The liquid laundry detergent composition comprises a core/shell encapsulate, wherein the core comprises a benefit agent and wherein the shell comprises polyacrylate, polyurethane, polyurea or a mixture thereof. The core/shell encapsulate is described in more detail below.

The liquid laundry detergent composition comprises a free perfume, wherein the free perfume comprises an aldehydic perfume raw material, a ketone perfume raw material or a mixture thereof. The free perfume is described in more detail below.

The liquid laundry detergent composition comprises an alkanolamine. The alkanolamine may be selected from monoethanolamine, diethanolamine, triethanolamine or mixtures thereof. Preferably the alkanolamine is selected from monoethanolamine. The liquid laundry detergent composition may comprise between 1% and 15%, preferably between 2% and 12%, more preferably between 2.5% and 10% by weight of the liquid laundry detergent composition of the alkanolamine.

The liquid laundry detergent composition comprises sulphite. The sulphite preferably comprises sodium sulphite, calcium sulphite, potassium sulphite, magnesium sulphite, sodium bisulphite, calcium bisulphite, potassium bisulphite, magnesium bisulphite or a mixture thereof. The liquid laundry detergent composition may comprise from 0.01% to 1%, preferably from 0.05% to 0.8%, more preferably from 0.1% to 0.5% by weight of the liquid laundry detergent composition of sulfite.

The liquid laundry detergent composition comprises a $C_{11-13}$ linear alkylbenzene sulphonate. By 'linear', we herein mean the alkyl group is linear. Alkyl benzene sulfonates are well known in the art.

The liquid laundry detergent composition may comprises a non-ionic surfactant. Preferably, the non-ionic surfactant is selected from a fatty alcohol alkoxylate, an oxo-synthesised fatty alcohol alkoxylate, Guerbet alcohol alkoxylates, alkyl phenol alcohol alkoxylates or a mixture thereof.

The liquid laundry detergent composition may comprise a fatty acid, an alkyl sulphate, an alkoxylated alkyl sulphate or a mixture thereof.

Preferably the alkoxylated alkyl sulphate comprises an ethoxylated alkyl sulphate. Preferably, the ethoxylated alkyl sulphate comprises an average degree of ethoxylation of between 0.5 and 7, preferably between 1 and 5.

The liquid laundry detergent composition may comprise a cleaning or care polymer. Preferably, the cleaning or care polymer is selected from an ethoxylated polyethyleneimine, alkoxylated polyalkyl phenol, an amphiphilic graft copolymer, a polyester terephthalate, a hydroxyethylcellulose, a carboxymethylcellulose or a mixture thereof.

The liquid laundry detergent composition may comprise from 0.1% to 20%, preferably from 0.5% to 15% by weight of the liquid laundry detergent composition of water.

The liquid laundry detergent composition may have a pH in the range of 6 to 9, preferably 7 to 8.

Core/Shell Encapsulate

The liquid laundry detergent composition comprises a core/shell encapsulate. Core/shell encapsulates comprise an outer shell defining an inner space in which a benefit agent is held until rupture of the shell.

The shell comprises polyacrylate, polyurethane, polyurea or a mixture thereof, preferably a polyacrylate.

Preferably the shell comprises from 50% to 100%, more preferably from 70% to 100%, most preferably from 80% to 100% of the polyacrylate. Preferably the polyacrylate comprises a polyacrylate cross linked polymer.

Preferably, the shell comprises a polymer derived from a material that comprises one or more multifunctional acrylate moieties; preferably said multifunctional acrylate moiety is selected from group consisting of tri-functional acrylate, tetra-functional acrylate, penta-functional acrylate, hexa-functional acrylate, hepta-functional acrylate and mixtures thereof; and optionally a polyacrylate that comprises a moiety selected from the group consisting of an amine acrylate moiety, methacrylate moiety, a carboxylic acid acrylate moiety, carboxylic acid methacrylate moiety and combinations thereof.

Preferably, the ratio of material that comprises one or more multifunctional acrylate moieties to material that comprises one or more methacrylate moieties is 999:1 to 6:4, more preferably from 99:1 to 8:1, most preferably from 99:1 to 8.5:1.

The shell may comprise a polyurea which is preferably the reaction product of the polymerisation between at least one polyisocyanate comprising at least two isocyanate functional groups and at least one amine, preferably a polyamine reactant selected from the group consisting of a water soluble guanidine salt and guanidine, a colloidal stabilizer and perfume.

The core/shell encapsulate may comprise an emulsifier, wherein the emulsifier is preferably selected from anionic emulsifiers, nonionic emulsifiers, cationic emulsifiers or mixtures thereof, preferably anionic emulsifiers.

The core/shell encapsulate may comprise from 0.1% to 1.1% by weight of the core/shell encapsulate of polyvinyl alcohol. Preferably, the polyvinyl alcohol has at least one the following properties, or a mixture thereof:

(i) a hydrolysis degree from 55% to 99%;

(ii) a viscosity of from 40 mPa·s to 120 mPa·s in 4% water solution at 20° C.;

(iii) a degree of polymerization of from 1,500 to 2,500;

(iv) number average molecular weight of from 65,000 Da to 110,000 Da.

Preferably the core/shell encapsulate have a volume weighted mean particle size from 0.5 microns to 100 microns, preferably from 1 micron to 60 microns.

The core of the core/shell encapsulate may comprise greater than 10% by weight of the core of a partitioning modifier. Preferably, the portioning modifier comprises a material selected from the group consisting of propan-2-yl tetradecanoate, vegetable oil, modified vegetable oil and mixtures thereof. Preferably, said modified vegetable oil is esterified and/or brominated. Preferably said partitioning modifier comprises propan-2-yl tetradecanoate.

The liquid laundry detergent composition may comprise between 0.1% and 25%, preferably between 0.2% and 20%, more preferably between 0.5% and 10%, most preferably between 0.75% and 5% by weight of the liquid laundry detergent composition of the benefit agent.

The benefit agent may comprise a perfume, an enzyme or mixture thereof. Preferably the benefit agent comprises a perfume.

The benefit agent may comprise a perfume, preferably wherein the perfume comprises by weight of said perfume from 2.5% to 30%, preferably from 5% to 30% of perfume raw materials characterized by a log P lower than 3.0, and a boiling point lower than 250° C., from 5% to 30%, preferably from 7% to 25% of perfume raw material characterized by a log P lower than 3.0 and a boiling point higher than 250° C., from 35% to 60%, preferably from 40% to 55% of perfume raw materials characterized by a log P higher than 3.0 and a boiling point lower than 250° C., from 10% to 45%, preferably from 12% to 40% of perfume raw materials characterized by log P higher than 3.0 and a boiling point higher than 250° C.

Free Perfume Composition:

The liquid laundry detergent may comprise between 0.0005% and 0.5%, preferably between 0.5% and 3%, more preferably between 0.9% and 2.5% by weight of the liquid laundry detergent composition of the free perfume composition wherein the free perfume comprises an aldehydic perfume raw material, a ketone perfume raw material or a mixture thereof.

Preferably, the liquid laundry detergent composition comprises between 0.0005% and 0.125%, more preferably between 0.0005% and 0.1%, even more preferably between 0.0005% and 0.05% by weight of the free perfume of the aldehydic perfume raw material, the ketone perfume raw material or a mixture thereof.

Preferably, the aldehydic perfume raw material, ketone perfume raw material or mixture thereof is selected from (2E,6E)-nona-2,6-dienal, 2,6,10-trimethylundec-9-enal; 1-methyl-4-(4-methylpent-3-enyl)cyclohex-3-ene-1-carbaldehyde; (E)-1-(2,6,6-trimethyl-1-cyclohex-2-enyl)but-2-en-1-one; (E)-4-(2,6,6-trimethyl-1-cyclohex-2-enyl)but-3-en-2-one; 2-benzylideneheptanal; (E)-1-(2,6,6-trimethyl-1-cyclohexenyl)but-2-en-1-one; 4-(2,6,6-trimethylcyclohexen-1-yl)but-3-en-2-one; 3-(4-tert-butylphenyl)propanal; (2Z)-2-benzylidenehexanal; 3-(4-methoxyphenyl)-2-methylpropanal; 3,7-dimethylocta-2,6-dienal; 2-(3,7-dimethyloct-6-enoxy)acetaldehyde; 3-(4-propan-2-ylphenyl)propanal; 3-(4-propan-2-ylphenyl)butanal; (E)-1-(2,6,6-trimethyl-1-cyclohexa-1,3-dienyl)but-2-en-1-one; 1-(2,6,6-trimethyl-1-cyclohex-3-enyl)but-2-en-1-one; 4-ethoxy-3-hydroxybenzaldehyde; 5-methylhept-2-en-4-one; 3-(2-ethylphenyl)-2,2-dimethylpropanal; 3-(3-isopropylphenyl)butanal; 1-(5,5-dimethyl-1-cyclohexenyl)pent-4-en-1-one; (E)-3-methyl-4-(2,6,6-trimethyl-1-cyclohex-2-enyl)but-3-en-2-one; 3-(1,3-benzodioxol-5-yl)-2-methylpropanal; 1,3-benzodioxole-5-carbaldehyde; 2-(phenylmethylidene)octanal; (E)-1-(2,4,4-trimethylcyclohex-2-en-1-yl)but-2-en-1-one; 3-(4-methyl-1-cyclohex-3-enyl)butanal; 2,6-dimethylhept-5-enal; 6-methylhept-5-en-2-one; methylphenyl[methylidene]heptanal; 5,5-dimethyl-2,3,4,4a,6,7-hexahydro-1H-naphthalene-2-carbaldehyde; 2-[2-(4-methyl-1-cyclohex-3-enyl)propyl]cyclopentan-1-one; 2,4-dimethylcyclohex-3-ene-1-carbaldehyde; undec-10-enal; 4-hydroxy-3-methoxybenzaldehyde; 4-methoxybenzaldehyde and mixtures thereof, preferably selected from the group comprising (E)-1-(2,6,6-trimethyl-1-cyclohex-2-enyl)but-2-en-1-one; (E)-4-(2,6,6-trimethyl-1-cyclohex-2-enyl)but-3-en-2-one; (E)-1-(2,6,6-trimethyl-1-cyclohexenyl)but-2-en-1-one; 4-(2,6,6-trimethylcyclohexen-1-yl)but-3-en-2-one; 3,7-dimethylocta-2,6-dienal; 3-(4-propan-2-ylphenyl)butanal; (E)-1-(2,6,6-trimethyl-1-cyclohexa-1,3-dienyl)but-2-en-1-one; 1-(2,6,6-trimethyl-1-cyclohex-3-enyl)but-2-en-1-one; 4-ethoxy-3-hydroxybenzaldehyde; 3-(2-ethylphenyl)-2,2-dimethylpropanal; 3-(3-isopropyl-phenyl)butanal; 1-(5,5-dimethyl-1-cyclohexenyl)pent-4-en-1-one; (E)-3-methyl-4-(2,6,6-trimethyl-1-cyclohex-2-enyl) but-3-en-2-one; 1,3-benzodioxole-5-carbaldehyde; 2-(phenylmethylidene)octanal; 2,4-dimethylcyclohex-3-ene-1-carbaldehyde; undec-10-enal; 4-hydroxy-3-methoxy-benzaldehyde; 4-methoxybenzaldehyde and mixtures thereof.

Preferably, the aldehydic perfume raw material is selected from (2E,6E)-nona-2,6-dienal, 2,6,10-trimethylundec-9-enal; 1-methyl-4-(4-methylpent-3-enyl)cyclohex-3-ene-1-carbaldehyde; 2-benzylideneheptanal; 3-(4-tert-butylphenyl)propanal; (2Z)-2-benzylidenehexanal; 3-(4-methoxyphenyl)-2-methylpropanal; 3,7-dimethylocta-2,6-dienal; 2-(3,7-dimethyloct-6-enoxy)acetaldehyde; 3-(4-propan-2-ylphenyl)propanal; 3-(4-propan-2-ylphenyl) butanal; 4-ethoxy-3-hydroxybenzaldehyde; 3-(2-ethylphenyl)-2,2-dimethylpropanal; 3-(3-isopropylphenyl) butanal; 3-(1,3-benzodioxol-5-yl)-2-methylpropanal; 1,3-benzodioxole-5-carbaldehyde; 2-(phenylmethylidene) octanal; 3-(4-methyl-1-cyclohex-3-enyl)butanal; 2,6-dimethylhept-5-enal; methylphenyl[methylidene]heptanal; 5,5-dimethyl-2,3,4,4a,6,7-hexahydro-1H-naphthalene-2-carbaldehyde; 2,4-dimethylcyclohex-3-ene-1-carbaldehyde; undec-10-enal; 4-hydroxy-3-methoxybenzaldehyde; 4-methoxybenzaldehyde and mixtures thereof, preferably selected from the group comprising 3,7-dimethylocta-2,6-dienal; 3-(4-propan-2-ylphenyl)butanal; 4-ethoxy-3-hydroxybenzaldehyde; 3-(2-ethylphenyl)-2,2-dimethylpropanal; 3-(3-isopropylphenyl)butanal; 1,3-benzodioxole-5-carbaldehyde; 2-(phenylmethylidene)octanal; 2,4-dimethylcyclohex-3-ene-1-carbaldehyde; undec-10-enal; 4-hydroxy-3-methoxybenzaldehyde; 4-methoxybenzaldehyde and mixtures thereof.

Preferably, the ketone perfume raw material is selected from (E)-1-(2,6,6-trimethyl-1-cyclohex-2-enyl)but-2-en-1-one; (E)-4-(2,6,6-trimethyl-1-cyclohex-2-enyl)but-3-en-2-one; (E)-1-(2,6,6-trimethyl-1-cyclohexenyl)but-2-en-1-one; 4-(2,6,6-trimethylcyclohexen-1-yl)but-3-en-2-one; (E)-1-(2,6,6-trimethyl-1-cyclohexa-1,3-dienyl)but-2-en-1-one; 1-(2,6,6-trimethyl-1-cyclohex-3-enyl)but-2-en-1-one; 5-methylhept-2-en-4-one; 1-(5,5-dimethyl-1-cyclohexenyl)pent-4-en-1-one; (E)-3-methyl-4-(2,6,6-trimethyl-1-cyclohex-2-enyl)but-3-en-2-one; (E)-1-(2,4,4-trimethylcyclohex-2-en-1-yl)but-2-en-1-one; 6-methylhept-5-en-2-one; 2-[2-(4-methyl-1-cyclohex-3-enyl)propyl]cyclopentan-1-one and mixtures thereof, preferably selected from the group comprising (E)-1-(2,6,6-trimethyl-1-cyclohex-2-enyl)but-2-en-1-one; (E)-4-(2,6,6-trimethyl-1-cyclohex-2-enyl)but-3-en-2-one; (E)-1-(2,6,6-trimethyl-1-cyclohexenyl)but-2-en-1-one; 4-(2,6,6-trimethylcyclohexen-1-yl)but-3-en-2-one; (E)-1-(2,6,6-trimethyl-1-cyclohexa-1,3-dienyl)but-2-en-1-one; 1-(2,6,6-trimethyl-1-cyclohex-3-enyl)but-2-en-1-one; 1-(5,5-dimethyl-1-cyclohexenyl)pent-4-en-1-one; (E)-3-methyl-4-(2,6,6-trimethyl-1-cyclohex-2-enyl)but-3-en-2-one and mixtures thereof.

The free perfume composition may comprise between 1% and 15%, preferably between 2% and 12.5% by weight of the free perfume composition of the ketone perfume raw material.

The free perfume composition may comprise between 0.1% and 15%, preferably between 0.25% and 10%, more preferably between 0.5% and 5% by weight of the free perfume composition of the aldehyde perfume raw material.

Structurant

The liquid laundry detergent composition may comprise a structurant. Suitable structurants are preferably ingredients which impart a sufficient yield stress or low shear viscosity to stabilize the liquid laundry detergent composition independently from, or extrinsic from, any structuring effect of the detersive surfactants of the composition. Preferably, they impart to the laundry detergent composition a high shear viscosity at 20 sec-1 at 21° C. of from 1 to 1500 cps and a viscosity at low shear (0.05 sec-1 at 21° C.) of greater than 5000 cps. The viscosity is measured using an AR 550 rheometer from TA instruments using a plate steel spindle at 40 mm diameter and a gap size of 500 µm. The high shear viscosity at 20 $s^{-1}$ and low shear viscosity at 0.5 $s^{-1}$ can be obtained from a logarithmic shear rate sweep from 0.1-1 to 25-1 in 3 minutes time at 21° C.

The structurant may be selected from non-polymeric or polymeric structurants. The structurant may be a non-polymeric structurant, preferably a crystallisable glyceride. The structurant may be a polymeric structurant, preferably a fibre based polymeric structurant, more preferably a cellulose fibre-based structurant. The structurant may be selected from crystallisable glyceride, cellulose-fibre based structurants, $TiO_2$, silica and mixtures thereof.

Said non-polymeric crystalline, hydroxyl functional structurants generally may comprise a crystallizable glyceride which can be pre-emulsified to aid dispersion into the final fluid detergent composition. In one aspect, crystallizable glycerides may include hydrogenated castor oil or "HCO" or derivatives thereof, provided that it is capable of crystallizing in the liquid detergent composition.

The liquid laundry detergent composition may comprise a naturally derived and/or synthetic polymeric structurant. Examples of naturally derived polymeric structurants of use in the present invention include: hydroxyethyl cellulose, hydrophobically modified hydroxyethyl cellulose, carboxymethyl cellulose, polysaccharide derivatives and mixtures thereof. Suitable polysaccharide derivatives include: pectine, alginate, arabinogalactan (gum Arabic), carrageenan, gellan gum, xanthan gum, guar gum and mixtures thereof. Examples of synthetic polymeric structurants of use in the present invention include: polycarboxylates, polyacrylates, hydrophobically modified ethoxylated urethanes, hydrophobically modified non-ionic polyols and mixtures thereof. In one aspect, said polycarboxylate polymer is a polyacrylate, polymethacrylate or mixtures thereof. In another aspect, the polyacrylate is a copolymer of unsaturated mono- or di-carbonic acid and $C_1$-$C_{30}$ alkyl ester of the (meth)acrylic acid. Said copolymers are available from Noveon Inc under the tradename Carbopol Aqua 30.

The structurant may comprise a fibre-based structurant. The structurant may comprise a microfibrillated cellulose (MFC), which is a material composed of nanosized cellulose fibrils, typically having a high aspect ratio (ratio of length to cross dimension). Typical lateral dimensions are 1 to 100, or 5 to 20 nanometres, and longitudinal dimension is in a wide range from nanometres to several microns. For improved structuring, the microfibrillated cellulose preferably has an average aspect ratio (l/d) of from 50 to 200,000, more preferably from 100 to 10,000. Microfibrillated cellulose can be derived from any suitable source, including bacterial cellulose, citrus fibers, and vegetables such as sugar beet, chicory root, potato, carrot, and the like. Said cellulosic fiber may be extracted from vegetables, fruits or wood. Commercially available examples are Avicel® from FMC, Citri-Fi from Fiberstar, Betafib from Cosun or Exilva from Borregaard.

Water-Soluble Unit Dose Article

A further aspect of the present invention is a water-soluble unit dose article comprising a water-soluble film and a liquid laundry detergent composition according to the present invention. Preferably, the water-soluble film comprises polyvinylalcohol.

The water-soluble unit dose article comprises at least one water-soluble film shaped such that the unit-dose article comprises at least one internal compartment surrounded by the water-soluble film. Then at least one compartment comprises the liquid laundry detergent composition. The water-soluble film is sealed such that the liquid laundry detergent composition does not leak out of the compartment during storage. However, upon addition of the water-soluble unit dose article to water, the water-soluble film dissolves and releases the contents of the internal compartment into the wash liquor.

The compartment should be understood as meaning a closed internal space within the unit dose article, which holds the liquid laundry detergent. Preferably, the unit dose article comprises a water-soluble film. The unit dose article is manufactured such that the water-soluble film completely surrounds the liquid laundry detergent composition and in doing so defines the compartment in which the liquid laundry detergent resides. The unit dose article may comprise two films. A first film may be shaped to comprise an open compartment into which the liquid laundry detergent is added. A second film is then laid over the first film in such an orientation as to close the opening of the compartment. The first and second films are then sealed together along a seal region. The water-soluble film is described in more detail below.

The unit dose article may comprise more than one compartment, even at least two compartments, or even at least three compartments. The compartments may be arranged in superposed orientation, i.e. one positioned on top of the other. Alternatively, the compartments may be positioned in a side-by-side orientation, i.e. one orientated next to the other. The compartments may even be orientated in a 'tyre and rim' arrangement, i.e. a first compartment is positioned next to a second compartment, but the first compartment at least partially surrounds the second compartment, but does not completely enclose the second compartment. Alternatively one compartment may be completely enclosed within another compartment.

Wherein the unit dose article comprises at least two compartments, one of the compartments may be smaller than the other compartment. Wherein the unit dose article comprises at least three compartments, two of the compartments may be smaller than the third compartment, and preferably the smaller compartments are superposed on the larger compartment. The superposed compartments preferably are orientated side-by-side.

In a multi-compartment orientation, the liquid laundry detergent according to the present invention may be comprised in at least one of the compartments. It may for example be comprised in just one compartment, or may be comprised in two compartments, or even in three compartments.

Each compartment may comprise the same or different compositions. The different compositions could all be in the same form, or they may be in different forms.

The water-soluble unit dose article may comprise at least two internal compartments, wherein the liquid laundry detergent composition is comprised in at least one of the compartments, preferably wherein the unit dose article comprises at least three compartments, wherein the liquid laundry detergent composition is comprised in at least one of the compartments.

The film of the present invention is soluble or dispersible in water and comprises at least one polyvinylalcohol or a copolymer thereof. Preferably, the water-soluble film comprises a blend of at least two different polyvinylalcohol homopolymers, at least two different polyvinylalcohol copolymers, at least one polyvinylalcohol homopolymer and at least one polyvinylalcohol copolymer or a combination thereof.

The water-soluble film preferably has a thickness of from 20 to 150 micron, preferably 35 to 125 micron, even more preferably 50 to 110 micron, most preferably from about 70 to 90 microns especially about 76 micron. By film thickness, we herein mean the thickness of the film prior to any deformation during manufacture.

Preferably, the film has a water-solubility of at least 50%, preferably at least 75% or even at least 95%, as measured by the method set out here after using a glass-filter with a maximum pore size of 20 microns:

5 grams±0.1 gram of film material is added in a pre-weighed 3 L beaker and 2 L±5 ml of distilled water is added. This is stirred vigorously on a magnetic stirrer, Labline model No. 1250 or equivalent and 5 cm magnetic stirrer, set at 600 rpm, for 30 minutes at 30° C. Then, the mixture is filtered through a folded qualitative sintered-glass filter with a pore size as defined above (max. 20 micron). The water is dried off from the collected filtrate by any conventional method, and the weight of the remaining material is determined (which is the dissolved or dispersed fraction). Then, the percentage solubility or dispersability can be calculated.

Preferred film materials are preferably polymeric materials. The film material can, for example, be obtained by casting, blow-moulding, extrusion or blown extrusion of the polymeric material, as known in the art.

Preferred polymers, copolymers or derivatives thereof suitable for use as pouch material are selected from polyvinyl alcohols, polyvinyl pyrrolidone, polyalkylene oxides, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatine, natural gums such as xanthum and carragum. More preferred polymers are selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and most preferably selected from polyvinyl alcohols, polyvinyl alcohol copolymers and hydroxypropyl methyl cellulose (HPMC), and combinations thereof. Preferably, the level of polymer in the pouch material, for example a PVA polymer, is at least 60%. The polymer can have any weight average molecular weight, preferably from about 1000 to 1,000,000, more preferably from about 10,000 to 300,000 yet more preferably from about 20,000 to 150,000.

Preferably, the water-soluble unit dose article comprises polyvinylalcohol.

Mixtures of polymers can also be used as the pouch material. This can be beneficial to control the mechanical and/or dissolution properties of the compartments or pouch, depending on the application thereof and the required needs. Suitable mixtures include for example mixtures wherein one polymer has a higher water-solubility than another polymer, and/or one polymer has a higher mechanical strength than another polymer. Also suitable are mixtures of polymers having different weight average molecular weights, for example a mixture of PVA or a copolymer thereof of a weight average molecular weight of about 10,000-40,000, preferably around 20,000, and of PVA or copolymer thereof, with a weight average molecular weight of about 100,000 to 300,000, preferably around 150,000. Also suitable herein are polymer blend compositions, for example comprising hydrolytically degradable and water-soluble polymer blends such as polylactide and polyvinyl alcohol, obtained by mixing polylactide and polyvinyl alcohol, typically comprising about 1-35% by weight polylactide and about 65% to 99% by weight polyvinyl alcohol.

Preferred for use herein are PVA polymers which are from about 60% to about 98% hydrolysed, preferably about 80% to about 90% hydrolysed, to improve the dissolution characteristics of the material.

Preferred films exhibit good dissolution in cold water, meaning unheated distilled water. Preferably such films exhibit good dissolution at temperatures of 24° C., even more preferably at 10° C. By good dissolution it is meant that the film exhibits water-solubility of at least 50%, preferably at least 75% or even at least 95%, as measured by the method set out here after using a glass-filter with a maximum pore size of 20 microns, described above.

Preferred films are those supplied by Monosol.

Of the total PVA resin content in the film described herein, the PVA resin can comprise about 30 to about 85 wt % of the first PVA polymer, or about 45 to about 55 wt % of the first PVA polymer. For example, the PVA resin can contain about 50 w. % of each PVA polymer, wherein the viscosity of the first PVA polymer is about 13 cP and the viscosity of the second PVA polymer is about 23 cP, measured as a 4% polymer solution in demineralized water at 20° C.

Preferably the film comprises a blend of at least two different polyvinylalcohol homopolymers and/or copolymers.

Most preferably the water soluble film comprises a blend of at least two different polyvinylalcohol homopolymers, especially a water soluble film comprising a blend of at least two different polyvinylalcohol homopolymers of different average molecular weight, especially a blend of 2 different polyvinylalcohol homopolymers having an absolute average viscosity difference $|\mu_2-\mu_1|$ for the first PVOH homopolymer and the second PVOH homopolymer, measured as a 4% polymer solution in demineralized water, in a range of 5 cP to about 15 cP, and both homopolymers having an average degree of hydrolysis between 85% and 95% preferably between 85% and 90%. The first homopolymer preferably has an average viscosity of 10 to 20 cP preferably 10 to 15 cP The second homopolymer preferably has an average viscosity of 20 to 30 cP preferably 20 to 25 cP. Most preferably the two homopolymers are blended in a 40/60 to a 60/40 weight % ratio.

Alternatively the water soluble film comprises a polymer blend comprising at least one copolymer comprising polyvinylalcohol and anionically modified monomer units. In particular the polymer blend might comprise a 90/10 to 50/50 weight % ratio of a polyvinylalcohol homopolymer and a copolymer comprising polyvinylalcohol and anionically modified monomer units. Alternatively the polymer blend might comprise a 90/10 to 10/90 weight % ratio of two different copolymers comprising polyvinylalcohol and anionically modified monomer units.

General classes of anionic monomer units which can be used for the PVOH copolymer include the vinyl polymerization units corresponding to monocarboxylic acid vinyl monomers, their esters and anhydrides, dicarboxylic monomers having a polymerizable double bond, their esters and anhydrides, vinyl sulfonic acid monomers, and alkali metal salts of any of the foregoing. Examples of suitable anionic monomer units include the vinyl polymerization units corresponding to vinyl anionic monomers including vinyl acetic acid, maleic acid, monoalkyl maleate, dialkyl maleate, monomethyl maleate, dimethyl maleate, maleic anyhydride, fumaric acid, monoalkyl fumarate, dialkyl fumarate, monomethyl fumarate, dimethyl fumarate, fumaric anyhydride, itaconic acid, monomethyl itaconate, dimethyl itaconate, itaconic anhydride, vinyl sulfonic acid, allyl sulfonic acid, ethylene sulfonic acid, 2-acrylamido-1-methylpropanesulfonic acid, 2-acrylamido-2-methylpropanesulfonic acid, 2-methylacrylamido-2-methylpropanesulfonic acid, 2-sufoethyl acrylate, alkali metal salts of the foregoing (e.g., sodium, potassium, or other alkali metal salts), esters of the foregoing (e.g., methyl, ethyl, or other $C_1$-$C_4$ or $C_6$ alkyl esters), and combinations thereof (e.g., multiple types of anionic monomers or equivalent forms of the same anionic monomer). In an aspect, the anionic monomer can be one or more acrylamido methylpropanesulfonic acids (e.g., 2-acrylamido-1-methylpropanesulfonic acid, 2-acrylamido-2-methylpropanesulfonic acid, 2-methylacrylamido-2-methylpropanesulfonic acid), alkali metal salts thereof (e.g., sodium salts), and combinations thereof. In an aspect, the anionic monomer can be one or more of monomethyl maleate, alkali metal salts thereof (e.g., sodium salts), and combinations thereof.

The level of incorporation of the one or more anionic monomer units in the PVOH copolymers is not particularly limited. In some aspects, the one or more anionic monomer units are present in a PVOH copolymer in an amount in a range of about 2 mol. % to about 10 mol. % (e.g., at least 2.0, 2.5, 3.0, 3.5, or 4.0 mol. % and/or up to about 3.0, 4.0, 4.5, 5.0, 6.0, 8.0, or 10 mol. % in various embodiments), individually or collectively.

Naturally, different film material and/or films of different thickness may be employed in making the compartments of the present invention. A benefit in selecting different films is that the resulting compartments may exhibit different solubility or release characteristics.

The film material herein can also comprise one or more additive ingredients. For example, it can be beneficial to add plasticisers, for example glycerol, ethylene glycol, diethyleneglycol, propylene glycol, dipropylene glycol, sorbitol and mixtures thereof. Other additives may include water and functional detergent additives, including surfactant, to be delivered to the wash water, for example organic polymeric dispersants, etc.

The film may be opaque, transparent or translucent. The film may comprise a printed area. The printed area may cover between 10 and 80% of the surface of the film; or between 10 and 80% of the surface of the film that is in contact with the internal space of the compartment; or between 10 and 80% of the surface of the film and between 10 and 80% of the surface of the compartment.

The area of print may cover an uninterrupted portion of the film or it may cover parts thereof, i.e. comprise smaller areas of print, the sum of which represents between 10 and 80% of the surface of the film or the surface of the film in contact with the internal space of the compartment or both.

The area of print may comprise inks, pigments, dyes, blueing agents or mixtures thereof. The area of print may be opaque, translucent or transparent.

The area of print may comprise a single colour or maybe comprise multiple colours, even three colours. The area of print may comprise white, black, blue, red colours, or a mixture thereof. The print may be present as a layer on the surface of the film or may at least partially penetrate into the film. The film will comprise a first side and a second side. The area of print may be present on either side of the film, or be present on both sides of the film. Alternatively, the area of print may be at least partially comprised within the film itself.

The area of print may comprise an ink, wherein the ink comprises a pigment. The ink for printing onto the film has preferably a desired dispersion grade in water. The ink may be of any color including white, red, and black. The ink may be a water-based ink comprising from 10% to 80% or from 20% to 60% or from 25% to 45% per weight of water. The ink may comprise from 20% to 90% or from 40% to 80% or from 50% to 75% per weight of solid.

The ink may have a viscosity measured at 20° C. with a shear rate of 1000 $s^{-1}$ between 1 and 600 cPs or between 50 and 350 cPs or between 100 and 300 cPs or between 150 and 250 cPs. The measurement may be obtained with a cone-plate geometry on a TA instruments AR-550 Rheometer.

The area of print may be achieved using standard techniques, such as flexographic printing or inkjet printing. Preferably, the area of print is achieved via flexographic printing, in which a film is printed, then moulded into the shape of an open compartment. This compartment is then filled with a detergent composition and a second film placed over the compartment and sealed to the first film. The area of print may be on either or both sides of the film.

Alternatively, an ink or pigment may be added during the manufacture of the film such that all or at least part of the film is coloured.

The film may comprise an aversive agent, for example a bittering agent. Suitable bittering agents include, but are not limited to, naringin, sucrose octaacetate, quinine hydrochloride, denatonium benzoate, or mixtures thereof. Any suitable level of aversive agent may be used in the film. Suitable levels include, but are not limited to, 1 to 5000 ppm, or even 100 to 2500 ppm, or even 250 to 2000 ppm.

Process of Washing Fabrics

A further aspect of the present invention is a process of washing fabrics comprising the steps of contacting the liquid laundry detergent composition or unit dose article according to the present invention with water such that the liquid laundry detergent composition is diluted in water by at least 400 fold to form a wash liquor, and contacting fabrics with said wash liquor.

Method of Making

Those skilled in the art will be aware of standard techniques that can be used to make the core/shell encapsulates. Preferably, the core/shell encapsulates are made by an interfacial polymerization process.

A preferred process of making the core/shell encapsulates comprises the steps of:

a) reacting an acrylate monomer and/or acrylate oligomer, preferably a methacrylate monomer and/or methacrylate oligomer, in a benefit agent with a composition comprising:
    i) an amine acrylate and/or methacrylate and a strong acid; or
    ii) a carboxylic acid acrylate and/or methacrylate monomer and a strong base; or
    iii) an amine acrylate and/or methacrylate monomer and a carboxylic acid acrylate and/or carboxylic acid methacrylate monomer to form a core composition,
b) forming an emulsion comprising said core composition, a surfactant, preferably wherein the surfactant is selected from anionic, cationic, neutral surfactants or a mixture thereof, and water;
c) curing said emulsion by applying a sufficient amount of thermal, UV, and/or electron beam energy to said emulsion to induce sufficient free-radical polymerization to form a core/shell encapuslate comprising said benefit agent and a shell comprising an acrylate, said shell encapsulating said benefit agent.

Suitable equipment for use may include continuous stirred tank reactors, homogenizers, turbine agitators, recirculating pumps, paddle mixers, ploughshear mixers, ribbon blenders, vertical axis granulators and drum mixers, both in batch and, where available, in continuous process configurations, spray dryers, and extruders. Such equipment can be obtained from Lodige GmbH (Paderborn, Germany), Littleford Day, Inc. (Florence, Ky., U.S.A.), Forberg AS (Larvik, Norway), Glatt Ingenieurtechnik GmbH (Weimar, Germany), Niro (Soeborg, Denmark), Hosokawa Bepex Corp. (Minneapolis, Minn., USA), Arde Barinco (New Jersey, USA).

Those skilled in the art will be aware of processes to make the liquid detergent composition of the present invention. Those skilled in the art will be aware of standard processes and equipment to make the liquid detergent compositions.

Those skilled in the art will be aware of standard techniques to make the unit dose article. Standard forming processes including but not limited to thermoforming and vacuum forming techniques may be used.

A preferred method of making the water-soluble unit dose article according to the present invention comprises the steps of moulding a first water-soluble film in a mould to form an open cavity, filling the cavity with the liquid detergent composition, laying a second film over the first film to close the cavity, and sealing the first and second films together to produce the water-soluble unit dose article.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Method to Quantify Encapsulated Perfume in Enapsulates.

To determine the identity and to quantify the weight of perfume, perfume ingredients, or Perfume Raw Materials (PRMs), encapsulated within the encapsulates, Gas Chromatography with Mass Spectroscopy/Flame Ionization Detector (GC-MS/FID) is employed. Suitable equipment includes: Agilent Technologies G1530A GC/FID; Hewlett Packard Mass Selective Device 5973; and 5%-Phenyl-methylpolysiloxane Column J&W DB-5 (30 m length×0.25 mm internal diameter×0.25 μm film thickness). Approximately 3 g of the finished product or suspension of encapsulates, is weighed and the weight recorded, then the sample is diluted with 30 mL of deionised water and filtered through a 5.0 μm pore size nitrocellulose filter membrane. Material captured on the filter is solubilized in 5 mL of an TD solution (25.0 mg/L tetradecane in anhydrous alcohol), and heated at 60° C. for 30 minutes. The cooled solution is filtered through a 0.45 μm pore size PTFE syringe filter and analyzed via Gas Chromatography with Mass Spectrometer detector/Flame Ionization Detector (GC-MS/FID). Three known perfume oils are used as comparison reference standards. Data Analysis involves summing the total area counts minus the TD area counts, and calculating an average Response Factor (RF) for the 3 standard perfumes. Then the Response Factor and total area counts for the product encapsulated perfumes are used along with the weight of the sample, to determine the total weight percent for each PRM in the encapsulated perfume. PRMs are identified from the mass spectrometry peaks.

Procedure for Determination of Percentage Perfume Leakage from an Encapsulate in Liquid Laundry Detergent Via Liquid-Liquid Extraction and GC-MS Analysis When determining the percentage perfume leakage from encapsulates in a liquid laundry detergent, a fresh liquid detergent with equal level of free perfume (without encapsulates) must also be analysed in parallel for reference.

1. Preparation of TD Solution

Stock solution of tonalid: Weigh 70 mg tonalid and add 20 ml hexane.

TD solution: Dilute 200 μl of stock solution in 20 ml hexane.

Mix to homogenize

2. Perfume Extraction from Liquid Laundry Detergent without Perfume Encapsulates (Reference)

Weigh 2 g of liquid laundry detergent into an extraction vessel (vial of 25 ml)

Add 2 ml of TD solution and close vessel

Extract perfume by gently turning the extraction vessel upside-down for 20 times (manually)

After separation of layers, immediately transfer hexane-layer into GC auto sampler-vial and cap vial Inject splitless (1.5 μl) into GC injection-port Run GC-MS analysis 3. Perfume Extraction from Liquid Laundry Detergent with Encapsulates Weigh 2 g of liquid laundry detergent into an extraction vessel (vial of 25 ml)

Add 2 ml of TD solution and close vessel

Extract perfume by gently turning the extraction vessel upside-down for 20 times (manually)

After separation of layers, immediately transfer hexane-layer into GC auto sampler-vial and cap vial Inject splitless (1.5 μl) into GC injection-port Run GC-MS analysis 4. Calculation The perfume leakage from encapsulates per individual perfume raw materials:

$$\% \text{ perfume leakage} = \frac{\text{Area } encap \times \text{Area } TD\ ref \times \text{Weight } ref \times 100}{\text{Area } TD\ encaps \times \text{Area } encaps\ ref \times \text{Weight } encaps}$$

Test Method for Determining the Logarithm of the Octanol/Water Partition Coefficient (log P)

The value of the log of the Octanol/Water Partition Coefficient (log P) is computed for each perfume raw material (PRM) in the perfume mixture being tested. The log P of an individual PRM is calculated using the Consensus log P Computational Model, version 14.02 (Linux) available from Advanced Chemistry Development Inc. (ACD/Labs) (Toronto, Canada) to provide the unitless log P value. The ACD/Labs' Consensus log P Computational Model is part of the ACD/Labs model suite.

Examples

The following are examples of unit dose executions wherein the liquid composition is enclosed within a PVA film. The preferred film used in the present examples is Monosol M8630 76 μm thickness.

| | Comparative example | | | Invention example | | |
|---|---|---|---|---|---|---|
| Compartment # | bottom | Top 1 | Top 2 | bottom | Top 1 | Top 2 |
| Dosage (g) | 25.7 | 1.71 | 1.71 | 25.7 | 1.71 | 1.71 |
| Ingredients (Wt %) | | | | | | |
| $C_{11-13}$ alkylbenzene sulfonic acid | 19 | 17 | 16 | 19 | 17 | 16 |
| $C_{12-14}$ alkyl 7-ethoxylate | 8 | 6 | 6 | 8 | 6 | 6 |
| $C_{14-15}$ alkyl 7-ethoxylate | 6 | 6 | 6 | 6 | 6 | 6 |
| $C_{12-14}$ alkyl ethoxy 3 sulfate | 5 | 8 | 8 | 5 | 8 | 8 |
| Citric acid | 0.7 | 0.6 | 0.6 | 0.7 | 0.6 | 0.6 |
| $C_{12-18}$ Fatty acid | 11 | 5 | 5 | 11 | 5 | 5 |
| Enzymes | 2 | — | — | 2 | — | — |
| Ethoxylated Polyethylenimine[1] | 3 | 5 | 5 | 3 | 5 | 5 |
| Hydroxyethane diphosphonic acid | 0.8 | 0.7 | 0.7 | 0.8 | 0.7 | 0.7 |
| Brightener | 0.3 | — | — | 0.3 | — | — |
| MgCl2 | 0.2 | 0.2 | 0.2 | 0.2 | 0.2 | 0.2 |
| Free Perfume[2] | 2.1 | — | — | 2.1 | — | — |
| $K_2SO_3$ | 0.4 | — | — | 0.4 | — | — |
| Perfume encapsulated in MF Microcapsules[3] | 0.40 | — | — | — | — | — |
| Perfume encapsulated in Polyacrylate Microcapsules[4] | — | — | — | 0.40 | — | — |
| Minors (antioxidant, aesthetics, structurant, opacifier, . . . ) | 2.0 | 2.0 | 2.0 | 2.0 | 2.0 | 2.0 |

-continued

| | Comparative example | | | Invention example | | |
|---|---|---|---|---|---|---|
| Compartment # | bottom | Top 1 | Top 2 | bottom | Top 1 | Top 2 |
| MonoEthanolamine to | pH 8 | pH 8 | pH 8 | pH 8 | pH 8 | pH 8 |
| Water and solvents (1,2 propanediol, glycerol, ethanol) to | 100% | 100% | 100% | 100% | 100% | 100% |

[1]Polyethylenimine (MW = 600) with 20 ethoxylate groups per —NH.

[2]Free perfume comprises 2.5% of total aldehyde and ketone Perfume Raw Materials.

[3]Melamine Formaldehyde (MF) perfume capsule coated with a polyvinylformamide deposition aid.

Suitable perfume capsules can be purchased from Encapsys, (825 East Wisconsin Ave, Appleton, WI 54911), and are made as follows: 25 grams of butyl acrylate-acrylic acid copolymer emulsifier (Colloid C351, 25% solids, pka 4.5-4.7, (Kemira Chemicals, Inc. Kennesaw, Georgia U.S.A.) is dissolved and mixed in 200 grams deionized water. The pH of the solution is adjusted to pH of 4.0 with sodium hydroxide solution. 8 grams of partially methylated methylol melamine resin (Cymel 385, 80% solids, (Cytec Industries West Paterson, New Jersey, U.S.A.)) is added to the emulsifier solution. 200 grams of perfume oil is added to the previous mixture under mechanical agitation and the temperature is raised to 50° C. After mixing at higher speed until a stable emulsion is obtained, the second solution and 4 grams of sodium sulfate salt are added to the emulsion. This second solution contains 10 grams of butyl acrylate-acrylic acid copolymer emulsifier (Colloid C351, 25% solids, pka 4.5-4.7, Kemira), 120 grams of distilled water, sodium hydroxide solution to adjust pH to 4.8, 25 grams of partially methylated methylol melamine resin (Cymel 385, 80% solids, Cytec). This mixture is heated to 85° C. and maintained overnight with continuous stirring to complete the encapsulation process. A volume-mean particle size of 18 microns is obtained. 14 milliliters of the aqueous suspension of perfume capsules obtained as per the above are placed in a 20 milliliter centrifuge tube. 6 identical tubes are prepared and placed in a batch centrifuge (IEC Centra CL2). After 20 minutes at 3800 RPM, the centrifuge tubes are removed, and three layers are observed: perfume capsule cake layer on top, followed by an aqueous layer, followed by a high density solid particulate layer. The top capsule layer is isolated from the remaining material, and reconstituted to make a phase stable suspension. To 20.8 grams of the top perfume capsule layer is added 10.6 grams of DI water, then 1.6 grams of urea (Potash Corporation), 6.0 grams of 1 wt % aqueous solution of Optixan Xanthan Gum (ADM Corporation), and 2.4 grams of 32 wt % magnesium chloride solution (Chemical Ventures). 0.5 grams of a cationic modified co polymer of poly vinylamine and N-vinyl formamide (BASF Corp) is added.

[4]Polyacrylate-based capsules encapsulating perfume.

Suitable perfume capsules can be purchased from Encapsys, (825 East Wisconsin Ave, Appleton, WI 54911), and are made as follows: a first oil phase, consisting of 37.5 g perfume, 0.2 g tert-butylamino ethyl methoacrylate, and 0.2 g beta hydroxyethyl acrylate is mixed for about 1 hour before the addition of 18 g CN975 (Sartomer, Exter, PA). The solution is allowed to mix until needed later in the process.

A second oil phase consisting of 65 g of the perfume oil, 84 g isopropyl myristate, 1 g 2,2'-azobis(2-methylbutyronitrile), and 0.8 g 4,4'-azobis[4-cyanovaleric acid] is added to a jacketed steel reactor. The reactor is held at 35° C. and the oil solution in mixed at 500 rpm's with a 2" flat blade mixer. A nitrogen blanket is applied to the reactor at a rate of 300 cc/min. The solution is heated to 70° C. in 45 minutes and held at 70° C. for 45 minutes, before cooling to 50° C. in 75 minutes. At 50° C., the first oil phase is added and the combined oils are mixed for another 10 minutes at 50° C.

A water phase, containing 85 g Celvol 540 PVA (Sekisui Specialty Chemicals, Dallas, TX) at 5% solids, 268 g water, 1.2 g 4,4'-azobis[4-cyanovaleric acid], and 1.1 g 21.5% NaOH, is prepared and mixed until the 4,4'-AZOBIS[4-CYANOVALERIC ACID] dissolves. The water phase pH for this batch was 4.90.

Once the oil phase temperature has decreased to 50° C., mixing is stopped and the water phase is added to the mixed oils. High shear agitation is applied to produce an emulsion with the desired size characteristics (1900 rpm's for 60 minutes.)

The temperature was increased to 75° C. in 30 minutes, held at 75° C. for 4 hours, increased to 95° C. in 30 minutes, and held at 95° C. for 6 hours. The batch was allowed to cool to room temperature.

Data

Leakage data in Table 1 show that leakage in presence of potassium sulfite ($K_2SO_3$) is minimized when the liquid composition comprises the benefit agent encapsulated in a polyacrylate-based capsule versus when the benefit agent is encapsulated in melamine formaldehyde (MF) based capsules.

TABLE 1

| Storage conditions | Coated MF perfume capsules and 0.40% $K_2SO_3$ | Polyacrylate-base perfume capsules and 0.40% $K_2SO_3$ |
|---|---|---|
| 20° C. - 2 Months | 9% | 3% |
| 20° C. - 6 Months | 26% | 4% |
| 40° C. - 2 Months | 30% | 6% |

Color stability data in Table 2 show that color stability in presence of potassium sulfite ($K_2SO_3$) is improved when the liquid composition comprises the benefit agent encapsulated in a polyacrylate-based capsule versus when the benefit agent is encapsulated in melamine formaldehyde (MF) based capsules.

The colour stability of the various compositon and perfume combinations was tested over time. Colour stability of the liquid laundry detergent compositions were tested by aging the test samples at 50° C. for 4 weeks. The colour of the fresh and aged sample were measured with a ColorQuest XE spectrophotometer by HunterLab and L*, a*- and b*-values. The delta b*(Δb) values were calculated for aged versus fresh samples. Spectrophotometric measurement were conducted as fresh and at 4 weeks.

TABLE 2

| color stability upon 4 weeks storage at 50° C. | | |
|---|---|---|
| Storage conditions | Coated MF perfume capsules and 0.40% $K_2SO_3$ | Polyacrylate-base perfume capsules and 0.40% $K_2SO_3$ |
| Δb | 6.06 | 1.87 |

A larger positive change in b, Δb, means that the composition with coated melamine formaldehyde capsules has discoloured towards yellow more than the composition with polyacrylate based perfume capsules.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition of the same term in a document incorporated by reference, the meaning of definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid laundry detergent composition comprising:

a. a core/shell encapsulate, wherein the core comprises a benefit agent wherein the benefit agent comprises a perfume, wherein the perfume comprises by weight of said perfume:

from 2.5% to 30% of perfume raw materials characterized by a log P lower than 3.0 and a boiling point lower than 250° C., from 5% to 30% of perfume raw material characterized by a log P lower than 3.0 and a boiling point higher than 250° C., from 35% to 60% of perfume raw materials characterized by a log P higher than 3.0 and a boiling point lower than 250° C., and from 10% to 45% of perfume raw materials characterized by log P higher than 3.0 and a boiling point higher than 250° C., and wherein the shell comprises polyacrylate, polyurethane, polyurea or a mixture thereof;

b. free perfume, wherein the free perfume comprises an aldehydic perfume raw material, a ketone perfume raw material or a mixture thereof;

c. an alkanolamine;

d. sulphite;

e. a $C_{11-13}$ linear alkylbenzene sulphonate.

2. The liquid laundry detergent composition according to claim 1 comprising between about 0.1% and about 25% by weight of the liquid laundry detergent composition of the benefit agent.

3. The liquid laundry detergent composition according to claim 1 wherein the shell comprises from about 50% to about 100% of the polyacrylate.

4. The liquid laundry detergent composition according to claim 1 wherein the polyacrylate comprises a polyacrylate cross linked polymer derived from a material that comprises one or more multifunctional acrylate moieties.

5. The liquid laundry detergent composition according to claim 4 wherein the multifunctional acrylate moiety is selected from the group consisting of tri-functional acrylate, tetra- functional acrylate, penta-functional acrylate, hexa-functional acrylate, hepta-functional acrylate and mixtures thereof, wherein the polyacrylate comprises a moiety selected from the group consisting of an amine acrylate moiety, methacrylate moiety, a carboxylic acid acrylate moiety, carboxylic acid methacrylate moiety and combinations thereof.

6. The liquid laundry detergent composition according to claim 1 comprising between about 0.0005 and about 5%, by weight of the liquid laundry detergent composition of the free perfume composition, wherein the liquid laundry detergent composition comprises between about 0.0005 and about 0.125%, by weight of the free perfume of the aldehydic perfume raw material, ketone perfume raw material or a mixture thereof.

7. The liquid laundry detergent composition according to claim 1 wherein the aldehydic perfume raw material, ketone perfume raw material or mixture thereof is selected from (2E,6E)-nona-2,6-dienal, 2,6,10-trimethylundec-9-enal; 1-methyl-4-(4-methylpent-3-enyl)cyclohex-3-ene-1-carbaldehyde; (E)-1-(2,6,6-trimethyl-1-cyclohex-2-enyl)but-2-en-1-one; (E)-4-(2,6,6-trimethyl-1-cyclohex-2-enyl)but-3-en-2-one; 2-benzylideneheptanal; (E)-1-(2,6,6-trimethyl-1-cyclohexenyl)but-2-en-1-one; 4-(2,6,6-trimethylcyclohexen-1-yl)but-3-en-2-one; 3-(4-tert-butylphenyl)propanal, (2Z)-2-benzylidenehexanal; 3-(4-methoxyphenyl) -2-methylpropanal; 3,7-dimethylocta-2,6-dienal; 2-(3,7-dimethyloct-6-enoxy)acetaldehyde; 3-(4-propan-2-ylphenyl)propanal; 3-(4-propan-2-ylphenyl) butanal; (E)-1-(2,6,6-trimethyl-1-cyclohexa-1,3-dienyl)but-2-en-1-one; 1-(2,6,6-trimethyl-1-cyclohex-3-enyl)but-2-en-1-one; 4-ethoxy-3-hydroxybenzaldehyde; 5-methylhept-2-en-4-one; 3-(2-ethylphenyl)-2,2-dimethylpropanal; 3-(3-isopropylphenyl)butanal; 1-(5,5-dimethyl-1-cyclohexenyl) pent-4-en-1-one; (E)-3-methyl-4-(2,6,6-trimethyl-1-cyclohex-2-enyl)but-3-en-2-one; 3-(1,3-benzodioxol-5-yl)-2-methylpropanal; 1,3-benzodioxole-5-carbaldehyde; 2-(phenylmethylidene)octanal; (E)-1-(2,4,4-trimethylcyclohex-2-en-1-yl)but-2-en-1-one; 3-(4-methyl-1-cyclohex-3-enyl)butanal; 2,6-dimethylhept-5-enal; 6-methylhept-5-en-2-one; methylphenyl)methylidene]heptanal; 5,5-dimethyl-2, 3,4,4a,6,7-hexahydro-1H -naphthalene-2-carbaldehyde; 2-[2-(4-methyl-1-cyclohex-3-enyl)propyl]cyclopentan-1-one; 2,4-dimethylcyclohex-3-ene-1-carbaldehyde; undec-10-enal; 4-hydroxy-3-methoxybenzaldehyde; 4-methoxybenzaldehyde and mixtures thereof.

8. The liquid laundry detergent composition according to claim 1 wherein the alkanolamine is selected from monoethanolamine, diethanolamine, triethanolamine or mixtures thereof.

9. The liquid laundry detergent composition according to claim 1 wherein the liquid laundry detergent composition comprises between about 1% and about 15%, by weight of the liquid laundry detergent composition of the alkanolamine.

10. The liquid laundry detergent composition according to claim 1 comprising from about 0.01% to about 1%, by weight of the liquid laundry detergent composition of sulfite.

11. The liquid laundry detergent composition according to claim 10 wherein the sulphite comprises sodium sulphite, calcium sulphite, potassium sulphite, magnesium sulphite, bisulphite, sodium bisulphite, calcium bisulphite, potassium bisulphite, magnesium bisulphite or a mixture thereof.

12. The liquid laundry detergent composition according to claim 1 comprising a non-ionic surfactant, wherein the non-ionic surfactant is selected from a fatty alcohol alkoxylate, an oxo-synthesised fatty alcohol alkoxylate, Guerbet alcohol alkoxylates, alkyl phenol alcohol alkoxylates or a mixture thereof.

13. The liquid laundry detergent composition according to claim 1 comprising a fatty acid, an alkyl sulphate, an alkoxylated alkyl sulphate or a mixture thereof.

14. The liquid laundry detergent composition according to claim 1 comprising a cleaning or care polymer selected from an ethoxylated polyethyleneimine, alkoxylated polyalkyl phenol, an amphiphilic graft copolymer, a polyester terephthalate, a hydroxyethylcellulose, a carboxymethylcellulose or a mixture thereof.

15. The liquid laundry detergent composition according to claim 1 comprising from about 0.1% to about 20%, by weight of the liquid laundry detergent composition of water.

16. The liquid laundry detergent composition according to claim 1 having a pH in the range of about 6 to about 9.

17. A water-soluble unit dose article comprising a water-soluble film and a liquid laundry detergent composition according to claim 1, wherein the water-soluble film comprises polyvinylalcohol.

18. A process of washing fabrics comprising the steps of contacting the liquid laundry detergent composition or unit dose article according to claim 1 with water such that the liquid laundry detergent composition is diluted in water by at least about 400 fold to form a wash liquor, and contacting fabrics with said wash liquor.

19. The liquid laundry detergent composition according to claim 1, wherein the perfume comprises (E)-1-(2,6,6-trimethyl-1-cyclohex-2-enyl)but-2-en-1-one; (E) -4-(2,6,6-trimethyl-1-cyclohex-2-enyl)but-3-en-2-one; (E)-1-(2,6,6-trimethyl-1-cyclohexenyl)but-2-en-1-one; 4-(2,6,6-trimethylcyclohexen-1-yl)but-3-en-2-one; 3,7-dimethylocta-2,6-dienal; 3-(4-propan-2-ylphenyl)butanal; (E)-1-(2,6,6-trimethyl-1-cyclohexa-1,3-dienyl)but-2-en-1-one; 1-(2,6,6-trimethyl-1-cyclohex -3-enyl)but-2-en-1-one; 4-ethoxy-3-hydroxybenzaldehyde; 3-(2-ethylphenyl)-2,2-dimethylpropanal; 3-(3-isopropylphenyl)butanal; 1-(5,5-dimethyl-1-cyclohexenyl)pent-4-en- 1-one; (E)-3-methyl-4-(2,6,6-trimethyl-1-cyclohex-2-enyl)but-3-en-2-one; 1,3-benzodioxole-5-carbaldehyde; 2-(phenylmethylidene) octanal; 2,4-dimethylcyclohex-3-ene-1-carbaldehyde; undec -10-enal; 4-hydroxy-3-methoxybenzaldehyde; 4-methoxybenzaldehyde, or mixtures thereof.

* * * * *